United States Patent [19]

Halpaap et al.

[11] 4,295,968

[45] Oct. 20, 1981

[54] SEPARATING MATERIALS FOR THIN LAYER CHROMATOGRAPHY AND THEIR PREPARATION

[75] Inventors: Herbert Halpaap, Jugenhein; Karl-Friedrich Krebs, Darmstadt, both of Fed. Rep. of Germany

[73] Assignee: Merck Patent Gesellschaft mit beschrankter Haftung, Darmstadt, Fed. Rep. of Germany

[21] Appl. No.: 888,595

[22] Filed: Mar. 20, 1978

[30] Foreign Application Priority Data

Mar. 19, 1977 [DE] Fed. Rep. of Germany ....... 2712113

[51] Int. Cl.³ .............................................. B01D 15/08
[52] U.S. Cl. ................................. 210/198.3; 427/204; 427/344
[58] Field of Search ........................... 210/756, 198.3; 427/203, 204, 333, 336, 344

[56] References Cited

U.S. PATENT DOCUMENTS

| | | | |
|---|---|---|---|
| 3,502,217 | 3/1970 | Bruckner et al. | 210/198 C |
| 3,535,265 | 10/1970 | Baron et al. | 210/198 C |
| 3,922,431 | 11/1975 | Radmacher et al. | 210/198 C |
| 3,987,058 | 10/1976 | Saunders et al. | 210/198 C |

OTHER PUBLICATIONS

Preparation and Characteristics of Chemically Bonded Thin-Layer Chromatographic Plates by Gilpin and Sisco in the Journal of Chromatography, vol. 124, 1976, pp. 257-264.

*Primary Examiner*—John Adee
*Attorney, Agent, or Firm*—Millen & White

[57] ABSTRACT

A separating material for thin-layer chromatography, comprising a substrate material coated with a thin sorbent layer, wherein the sorbent layer optionally contains a binder, an indicator, or both, is improved in that the sorbent layer has a surface modified by reacting the sorbent layer with a silanizing agent without the exclusion of moisture.

12 Claims, No Drawings

SEPARATING MATERIALS FOR THIN LAYER CHROMATOGRAPHY AND THEIR PREPARATION

BACKGROUND OF THE INVENTION

Thin-layer chromatography (TLC) has found increasingly wide-spread acceptance as a rapid method for micro- and ultramicro-analysis. This method has received special impetus by the development of high-pressure liquid chromatography (HPLC). Since the results obtained in TLC can frequently be applied directly to the HPLC technique, for example with respect to analysis periods, $R_f$ values, and eluents, TLC has most recently acquired an additional field of application, in addition to actual microanalysis, namely to serve as a so-called pilot technique for HPLC. This means that initially, with the aid of TLC, suitable separating conditions are determined very rapidly for a specific separation problem, and these conditions can then be substantially applied to HPLC.

However, such an application is possible only if the separating characteristics of plate and column are identical. Sorbents have been developed, however, specifically for HPLC, the surfaces of which are modified by organic groups. These surface-modified (e.g. "reversed-phase") sorbents possess entirely different separating properties from those of non-modified materials and make it possible to execute a multitude of separating operations heretofore infeasible, due to the stepped transitions, depending on the type of modification, ranging from the hydrophilic sorption agent to a material becoming increasingly more hydrophobic, especially in connection with silica gel. By the choice of the organic groups utilized for surface modification, a great variety of surface properties can be conventionally attained.

However, on account of the differing separation properties, it is impossible to apply the results obtained in TLC to these separating materials. Thus, with the objective of being able to utilize, on the one hand, TLC as the pilot technique even for sorbents having a chemically modified surface and of opening up, on the other hand, these variegated separating possibilities also for TLC analysis, the task was under taken of providing TLC separating materials which likewise contain sorbents modified by organic groups.

The attainment of this objective, however, met with considerable difficulties, since the reversed-phase sorbents known from HPLC are unsuitable for producing the customary instant TLC preparations. Such preparations, as is known, are TLC plates or films coated in the usual way with thin layers of the separating material, the latter normally containing binders and optionally indicators. Attempts at producing, by means of the conventional, chemically modified sorbents, TLC layers satisfactory with respect to separating characteristics, adhesive strength, and abrasion resistance have, however, met with failure.

The modified materials show very poor adhesion to the substrate material and cannot be processed with the usual binders.

Also, efforts have been made to react carefully dried, silica gel-coated thin-layer plates with alkyl trichlorosilanes in a chamber sealed off from the outside atmosphere and likewise being kept carefully free of moisture (cf. Journal of Chromatography, 124 [1978]: 257–264). During this step, a chemical modification of the silica gel layer was produced. Due to the complex measures which must be employed in this process on account of the notorious sensitivity to hydrolysis displayed by halosilanes, to keep the reagents as well as the reaction chamber absolutely anhydrous, the process is very expensive and also unsuitable for use on a large technical scale.

SUMMARY OF THE INVENTION

Thus, an object of this invention is to find a process making it possible to produce instant TLC preparations with chemically modified sorbent in a simple and rapid process which can, above all, likewise be conducted on a large technical scale.

It has now been found that especially advantageous results are surprisingly achieved by providing that, during the subsequent treatment of the layer of the customary instant TLC preparations with a silanizing agent customary for surface modification, the surrounding atmosphere and consequently also moisture have unhindered access to the reaction chamber during and after the reaction. In contrast to the above, a person skilled in the art would have conducted such a reaction under strict exclusion of moisture.

In accordance with this surprisingly simple procedure, products are obtained which, with respect to their quality, astonishingly surpass even the materials produced according to the conventional, much more expensive process.

Accordingly, this invention relates to a separating material for thin-layer chromatography, consisting of a substrate material coated with a thin layer of sorbent, the layer optionally containing additionally binders and/or indicators, characterized in that the sorbent has a surface modified by reacting the TLC layer, without exclusion of moisture, with a silanizing agent.

In particular, the invention relates to a separating material characterized in that the sorbent layer is modified by optionally substituted aryl, aralkyl, or alkyl groups of up to 20 carbon atoms.

The sorbents, in this connection, are preferably silica gel, kieselguhr, and aluminum oxide.

The invention furthermore concerns a process for the production of these separating materials, characterized in that the sorbent layer of a conventional TLC separating material with an unmodified surface is impregnated with a solution of a silanizing agent in an organic solvent and dried in the open air; and that subsequently a washing step is initially carried out with at least one aprotic solvent and then a washing step with at least one protonic solvent.

A process is preferred which is characterized in that the silanizing agent employed is an optionally substituted aryl, aralkyl, or alkyl halosilane of up to 20 carbon atoms.

DETAILED DISCUSSION

The separating materials produced according to the process of this invention exhibit excellent properties. Thus, the adhesive strength of the sorbent layer is comparable to that of normal TLC layers. Also the separating efficiency and the reproduceability of the separating operations are not negatively affected by the subsequent modification of the layer. Especially suitable sorbents amenable to such a modification are aluminum oxide, silica gel, and kieselguhr.

The quality of the separating material of this invention is essentially influenced by the quality of the unmodified separating material used as the starting material. For this reason, it is possible to employ, besides the customary instant preparations utilized in TLC, preferably high-efficiency separating material as described, for example, in DOS [German Unexamined Laid-Open Application] No. 2,524,065. With regard to the substrate materials, the structure of the layers, and any optional additives, such as indicators and binders, there is no difference as compared to the conventional, unmodified separating materials.

The TLC separating materials of this invention can be produced in a surprising and highly simple way. A person skilled in the art of conducting silanizing processes and being aware of the high requirements with respect to uniformity and density of the surface coating, knows that such reactions take place successfully only under conditions which must be accurately maintained. Among these conditions is especially the need that the reaction take place in a protective gas atmosphere under the complete exclusion of moisture. While such conditions can be maintained relatively simply during the modification of sorbents not applied to plates or films, in customary devices, this is possible for instant preparations only under considerable expense, and these difficulties were apt to deter a person skilled in the art from making any attempt at all to conduct a large-scale chemical modification of the sorbent layer of an already coated plate or film.

It has been the more surprising that, according to the process of this invention, i.e. without special measures and without a protective gas atmosphere, on the contrary, especially in the open air, the result has been an extremely satisfactory, uniform, and dense covering of the surface of the layer.

The process is conducted by impregnating and/or saturating the sorbent layer of a chemically unmodified instant TLC preparation used as the starting material with a solution of the silanizing agent used for the modification. This can be done, for example, by immersing the starting material in the solution of the silanizing agent, or spraying such solution on the starting material. The solvent employed is a customary solvent inert with respect to the silanizing agent used. Preferably, organic solvents are utilized with boiling points of between 30° and 180° C., e.g. chlorinated hydrocarbons, such as di- and trichloromethane and/or di- and trichloroethane, or aromatic or aliphatic hydrocarbons.

Suitable silanizing agents are actually all silanes likewise utilized for the production of sorbents for column chromatography. For example, silanes are used of the type $R-SiX_3$ wherein R is an optionally substituted alkyl, aryl, or aralkyl group and wherein each of the substituents X can represent halogen, alkoxy, or alkyl, but wherein at least one X per mole is alkoxy or halogen. Preferably, R is an optionally branched alkyl residue of up to 20 carbon atoms. Depending on the desired final use, the residues R can in all cases be substituted in a variety of ways. Suitable substituents, in this connection, are also above all polar groups, for example hydroxy, amino, epoxy, cyano, halogen, ammonium, sulfonium, or carboxy. Also, the alkyl or aralkyl chain proper can be interrupted by oxygen, sulfur, or nitrogen atoms. Silanizing agents are known in great numbers from the literature or can be prepared analogously to conventional methods. They are equally well suited for the process of this invention as for the known modifications of sorbent surfaces.

The amount of the silanizing agent employed for the surface modification is dependent above all of the thickness of the sorbent layer and the specific surface area of the sorbent used for the coating. To obtain a complete coverage of the hydroxy groups of the untreated sorbent, the silanizing agent should be employed in an amount of at least 10 $\mu$mole/m$^2$ of sorbent surface. However, preferably an excess of the silanizing agent will be employed, for example 0.1–1 mmole/m$^2$. Also a larger excess can be advantageous in certain instances.

The specific surface area of the sorbents ranges between about 1 and 1000 m$^2$/g., in most cases between 200 and 800 m$^2$/g. The process of this invention is nowise limited, however, by the above values.

After the impregnation with the silanizing agent solution, the separating materials are dried in the open air. In this procedure, a protective gas atmosphere is expressly avoided, so that especially the moisture contained in the air has unhindered access to the separating layer.

The thus-treated separating materials are conducted once or repeatedly through a cleaning bath to clean them and to remove excess silanizing agent. In this connection, the cleaning bath consists merely of an aprotic solvent or solvent mixture, e.g. a mixture of methylene chloride and benzene or toluene. Another drying step is advantageously executed thereafter, preferably simply by allowing the product to stand in the open air.

Subsequently, the separating materials are then conducted through a second cleaning bath containing a protonic solvent or solvent mixture, preferably an alcohol/water mixture. The alcohols used herein are preferably lower aliphatic alcohols.

Suitable starting materials are all customary separating materials with a TLC aluminum oxide, TLC silica gel, or TLC kieselguhr layer on substrates. Suitable substrates are all conventional materials, glass plates being preferred. However, also usable are foils, e.g. of aluminum or also synthetic resin films. The sorbent layer is applied to these substrate materials in the form of a spreadable, in most cases aqueous suspension by means of customary spreaders or coating units. Customarily, binders increasing the adhesive strength and abrasion resistance and/or indicators are added to this suspension.

In principle, all conventional binders are suitable. However, it has been found that surprisingly a particularly advantageous surface modification is attained by the use of organic binders, rather than utilizing gypsum as the binder in accordance with the prior-art process. Such organic binders are known per se and described in the literature, for example in German Pat. Nos. 1,442,446 and 1,517,929.

In this connection, especially preferred, and the subject of a special embodiment of the present invention, are polymers of acrylic and methacrylic acid, acrylic and methylacrylic acid esters, especially those with hydrophilic residues, ethylene-maleic acid copolymers, polyacrylamide, and polymethacrylamide, which can optionally also be substituted on the amide nitrogen by lower alkyl groups, as well as copolymers and/or mixed polymers of these materials and the salts thereof. These binders are normally added in amounts of 0.1 to about 10%.

Suitable indicators are all customary indicators. The most frequently employed indicator is a fluorescent indicator especially manganese-activated zinc silicate, absorbent at 254 nm. under UV light. The indicators are normally incorporated in amounts of about 0.5 –5% by weight, but it is also possible to omit an indicator entirely.

The layer thickness of the sorbent layer of the separating materials according to this invention ranges, as in case of the heretofore customary TLC separating materials, normally within a magnitude of 100–300μ. In exceptional cases or for special applications it is, however, also possible to produce separating materials with thinner or thicker layers.

After the drying step, the novel separating materials of this invention are ready for use. They are utilized, in principle, exactly as the heretofore customary TLC separating materials. However, differences exist in that the user, due to the fact that the surface modification can be varied in a controlled fashion, now has available a palette of separating materials permitting the choice of an optimum separating material even for difficult separating processes. In this way, the possibilities of applying TLC have been enriched.

A further advantage of the novel separating materials resides in that, due to the hydrophobic characteristic of the sorbent layer, there is hardly any tendency to absorb water in the open air so that in many cases it is unnecessary to effect an activation of the separating materials prior to their use. This has the additional advantage that, by means of the novel separating materials, reproducible results can be obtained even with a careless mode of operation, which is possible with the conventional separating materials only if a controlled activation takes place prior to use.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Two plate racks with respectively 13 commercially available, binder-containing TLC instant plates 20×20 cm. (silica gel on glass) are immersed for 30 minutes in a trough containing 20 l. of a 10% by weight solution of dimethyldichlorosilane in dichloromethane and are then dried for 12 hours in the open air. The thus-dried plates are dipped for 30 minutes into a mixture of dichloromethane and toluene in a volume ratio of 1:1, dried in the air for 12 hours, then dipped for 30 minutes into a mixture of methanol and water in a volume ratio of 1:1, and again dried in the air. The thus-obtained plates can be used directly for a reversed-phase TLC chromatography.

EXAMPLE 2

The procedure takes place analogously to Example 1, except that methyloctyldichlorosilane is used in place of dimethyldichlorosilane, and the step of dipping into dichloromethane/toluene for 30 minutes is conducted twice instead of once.

EXAMPLE 3

The procedure of Example 1 is followed, except that methyloctadecyldichlorosilane is utilized instead of dimethyldichlorosilane, and the step of dipping into dichloromethane/toluene for 30 minutes is performed three times instead of once.

EXAMPLE 4

A plate rack with 50 commercially available, binder-containing TLC instant plates 20×20 cm. (silica gel on glass) is immersed for 30 minutes in a trough containing 20 l. of a 10% by weight solution of diphenyldichlorosilane in toluene, dried for 1 hour in the open air, and again immersed for 30 minutes. Thereafter, the plates are washed respectively three times with toluene, twice with dichloromethane/methanol 1:1, and twice with acetone/water 1:1, and dried.

EXAMPLE 5

A synthetic resin silica gel TLC film (50 m. × 20 cm.), wound up with the aid of spacer means so that there is a spacing of at least 1 mm. between the individual windings, is dipped for 30 minutes into a 10% by weight solution of dimethyldichlorosilane, dried for 1 hour in the air, again dipped for 30 minutes, and thereafter washed and dried as described in Example 4.

The preceding examples can be repeated with similar sucess by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a separating material for thin-layer chromatography, comprising a substrate material having a coating thereon which coating comprises a thin sorbent layer, the improvement wherein the sorbent layer has a surface modified by reacting the sorbent layer with a silanizing agent without the exclusion of moisture.

2. A separating material of claim 1, wherein the sorbent layer is modified by aryl, substituted aryl, aralkyl, substituted aralkyl, alkyl or substituted alkyl groups, each of up to 20 carbon atoms.

3. (Amended) A separating material of claim 1, wherein the sorbent is silica gel.

4. A process for the production of a separating material for thin layer chromatography, comprising a substrate material having a coating thereon, which coating comprises a thin sorbent layer having a surface modified by reacting the sorbent layer with a silanizing agent without the exclusion of moisture,
   said process comprising impregnating the sorbent layer of a conventional TLC separating material with an unmodified surface with a solution of the silanizing agent in an organic solvent; drying the impregnated layer in air; subsequently washing the dried layer with at least one aprotic solvent; and then washing it with at least one protonic solvent.

5. A process of claim 4, wherein the silanizing agent is a methyl-alkyl, methyl-aryl, or methyl-aralkyl dichlorosilane with aryl, substituted aryl, aralkyl, substituted aralkyl, alkyl or substituted alkyl groups, each of up to 20 carbon atoms.

6. The separating material prepared by the process of claim 4 or 5.

7. The separating material of claim 1, wherein the sorbent is aluminum oxide, silica gel or kieselguhr.

8. The separating material of claim 1, wherein the binder is an organic binder.

9. The separating material of claim 1, wherein the sorbent layer further comprises a binder.

10. The separating material of claim 1, wherein the sorbent layer further comprises an indicator.

11. A separating material of claim 1 wherein the silanizing agent is a methyl-alkyl, methyl-aryl, or methyl-aralkyl dichlorosilane with aryl, substituted aryl, aralkyl, substituted aralkyl, alkyl or substituted alkyl groups, each of up to 20 carbon atoms.

12. The separating material of claim 1, wherein the sorbent layer has a surface modified by reacting the sorbent layer with a silanizing agent in the presence of air.

* * * * *